(12) United States Patent
Faure (10) Patent No.: US 11,052,117 B2
(45) Date of Patent: *Jul. 6, 2021

(54) USE OF A SWEET WHEY CONTAINING INFANT FORMULA FOR PROMOTING THE POSTNATAL NEURONAL DEVELOPMENT OF THE INFANT GASTROINTESTINAL TRACT, AND THE ESTABLISHMENT OF THE INTESTINAL FUNCTIONS THAT IT CONTROLS

(71) Applicant: NESTEC S.A., Vevey (CH)

(72) Inventor: Magali Faure, Forel (CH)

(73) Assignee: Societe des Produits Nestle S.A., Vevey (CH)

( * ) Notice: Subject to any disclaimer, the term of this patent is extended or adjusted under 35 U.S.C. 154(b) by 82 days.

This patent is subject to a terminal disclaimer.

(21) Appl. No.: 15/104,041

(22) PCT Filed: Dec. 12, 2014

(86) PCT No.: PCT/EP2014/077481
§ 371 (c)(1),
(2) Date: Jun. 13, 2016

(87) PCT Pub. No.: WO2015/086788
PCT Pub. Date: Jun. 18, 2015

(65) Prior Publication Data
US 2016/0310533 A1 Oct. 27, 2016

(30) Foreign Application Priority Data
Dec. 13, 2013 (EP) .................................. 13197197

(51) Int. Cl.
A61K 35/20 (2006.01)
A61K 35/745 (2015.01)
A23L 33/00 (2016.01)
A23L 33/19 (2016.01)
A61K 35/747 (2015.01)

(52) U.S. Cl.
CPC .............. *A61K 35/20* (2013.01); *A23L 33/19* (2016.08); *A23L 33/40* (2016.08); *A61K 35/745* (2013.01); *A61K 35/747* (2013.01); *A23V 2002/00* (2013.01)

(58) Field of Classification Search
CPC .................................................. A61K 35/747
See application file for complete search history.

(56) References Cited

U.S. PATENT DOCUMENTS

2007/0031537 A1 2/2007 Secretin
2012/0015077 A1 1/2012 Secretin
2012/0184483 A1 7/2012 Faure et al.
2012/0219526 A1 8/2012 Klassen et al.
2013/0280225 A1* 10/2013 Faure .................. A61K 31/702
424/93.45

FOREIGN PATENT DOCUMENTS

EP 2609813 7/2013
WO WO-0111990 A1 * 2/2001 ............. A23L 33/40
WO 2013057062 4/2013
WO 2013153071 A2 10/2013

OTHER PUBLICATIONS

Sharma et al.,. Assessomg dietary intake among infants and toddlers 0-24 months of age in Baltimore, Maryland, USA, Nutrition Journal 2013, 12:52.*
Fuda et al. "Recovery of Lactoferrin and Lactoperoxidase from Sweet Whey Using Colloidal Gas Aphrons (CGAs) Generated from an Anionic Surfactant, AOT" Biotechnol. Prog, 2004, vol. 20, pp. 514-525.
Fernandez et al., "Caseinomacropeptide behaviour in a whey protein fractionation process based on α-lactalbumin precipitation", Journal of Dairy Research, May 2011, vol. 78, No. 2, pp. 196-202.
Russian Office Action for corresponding Russian Application No. 2016128439 dated Aug. 31, 2018, (11 pages).
Gregory et al., "Update on Nutrition for Preterm and Full-Term Infants", Jognn-Clinical Issues, vol. 34, No. 1, 2005, pp. 98-108.
Russian Office Action for Appl No. 2016128439/04(044353) dated Jul. 17, 2019.
Office Action received for Chinese Patent Application No. 201480067166.3, dated Sep. 16, 2019, 06 pages (6 pages of English Translation).
Lai et al., "Research Progress of the Effect of Whey Protein on Infant Growth and Development", Food and Nutrition in China, vol. 17, Issue No. 9, 2011, pp. 67-71.
China Office Action Received for Application No. 201480067166.3, dated Apr. 7, 2020, 14 pages.

* cited by examiner

*Primary Examiner* — Bin Shen
(74) *Attorney, Agent, or Firm* — K&L Gates LLP (57) ABSTRACT

The present invention relates to administration of sweet whey protein (SWP) for promoting the enteric neuronal development in infants, especially preterm, low birth, very low and extremely low birth weight infants as well as in young children up until the age of six. Administration of the SWP according to the invention prevents and treats disorders associated with an immature or impaired enteric nervous system. The disorders are, notably, dysfunctional gastrointestinal motility manifested as slow intestinal transit, intestinal discomfort, hard stools, constipation and/or gastrointestinal reflux, gut barrier dysfunction, food intolerance or necrotizing enterocolitis.

18 Claims, 1 Drawing Sheet

USE OF A SWEET WHEY CONTAINING INFANT FORMULA FOR PROMOTING THE POSTNATAL NEURONAL DEVELOPMENT OF THE INFANT GASTROINTESTINAL TRACT, AND THE ESTABLISHMENT OF THE INTESTINAL FUNCTIONS THAT IT CONTROLS

CROSS REFERENCE TO RELATED APPLICATIONS

The present application is a National Stage of International Application No. PCT/EP2014/077481, filed on Dec. 12, 2014, which claims priority to European Patent Application No. 13197197.0, filed Dec. 13, 2013, the entire contents of which are being incorporated herein by reference.

FIELD OF THE INVENTION

The present invention relates generally to the field of neuronal health, neuronal protection and neuronal development. The invention specifically relates to administration of sweet whey protein for promoting the enteric neuronal development in infants, especially preterm, low birth, very low and extremely low birth weight infants.

BACKGROUND TO THE INVENTION

The nervous system is a highly complex network composed of neuronal and glial cells. It is present in all mammalian species and is composed of the central nervous system (brain and spinal cord) and the peripheral nervous system (somatic, autonomous and enteric nervous system).

The central nervous system drives the cognitive functions (memory, attention, perception, action, etc). Together with the peripheral nervous system, it has a fundamental role in the control of behaviour. The somatic nervous system is responsible for coordinating the body's movements (under conscious control). The autonomous nervous system maintains homeostasis in the body activities without conscious control (heart rate, etc). Finally, and as part of the latter system, the enteric nervous system directly controls the gastrointestinal tract functions. These include the gastrointestinal barrier and immune function, motility, absorption, digestion and exocrine/endocrine secretions, which contribute to the protection of the intestine from any type of injury and to digestive comfort [Neunlist, M. et al. (2008); Neuro-glial crosstalk in inflammatory bowel disease, *J Intern. Med*, 263: 577-583], [Burns, A. J. et al. (2009); Development of the enteric nervous system and its role in intestinal motility during fetal and early postnatal stages, *Semin. Pediatr. Surg.*, 18:196-205], [Tapper, E. J. (1983); Local modulation of intestinal ion transport by enteric neurons, *Am J Physiol.*, 244:G457-68].

The nervous system develops during gestation and then refines to a mature, functional network during the post natal period.

Because of the critical role of the enteric nervous system in the gastrointestinal function, the immaturity or delayed maturation of the nervous system will lead to delayed establishment and adequate functioning of major gastrointestinal functions. In particular, it will contribute to:

the immaturity of gastrointestinal motility [Burns, A. J. et al. (2009); Development of the enteric nervous system and its role in intestinal motility during fetal and early postnatal stages, Semin. Pediatr. Surg., 18:196-205], which will result in a slower intestinal transit with harder stools that will lead to intestinal discomfort and in more extreme cases to constipation, in increased predisposition of the infant to enteral feeding intolerance, the requirement of total parenteral nutrition, and in more severe cases to necrotizing enterocolitis (NEC) (Grave G D, Nelson S A, Walker W A, Moss R L, Dvorak B, Hamilton F A, Higgins R, Raju T N. New therapies and preventive approaches for necrotizing enterocolitis: report of a research planning workshop. Pediatr Res. 2007 October; 62(4):510-4; Indrio F, Riezzo G, Cavallo L, Di Mauro A, Francavilla R. Physiological basis of food intolerance in VLBW. J Matern Fetal Neonatal Med. 2011 October; 24 Suppl 1:64-6 the reduced digestive/absorptive intestinal capacity [Tapper, E. J. (1983); Local modulation of intestinal ion transport by enteric neurons, Am J Physiol., 244: G457-68]; Josef Neu & Liyan Zhang, Feeding intolerance in very low birth weight infants: What is it and what can we do about it? Acta Paediatrica 2005; 94 (suppl 449): 93-99]

the immaturity of the intestinal barrier function [Neunlist, M. et al. (2008); Neuro-glial crosstalk in inflammatory bowel disease, J Intern. Med, 263: 577-583, Burns, A. J. et al. (2009)], which increases the risks of infections, enteral feeding intolerance and necrotizing enterocolitis (NEC) [Athalye-Jape G, More K, Patole S Progress in the field of necrotising enterocolitis—year 2012. J Matern Fetal Neonatal Med. 2013 May; 26(7):625-32; Indrio F, Riezzo G, Cavallo L, Di Mauro A, Francavilla R. Physiological basis of food intolerance in VLBW. J Matern Fetal Neonatal Med. 2011 October; 24 Suppl 1:64-6]

An immature or impaired enteric nervous system can be observed in infants such as:

Preterm infants, low birth weight (<2500 g), very low birth weight infants (<1500 g) and extremely low birth weight (<1000 g); New J. Gastrointestinal development and meeting the nutritional needs of premature infants *Am J Clin Nutr* 2007; 85(2): 629S-634S.

Premature or term-born infants having experienced an intrauterine growth retardation (IUGR) that occurred following any adverse events during gestation (smoking of the mother, medication of the mother, low placenta quality, abnormal placenta positioning, malnutrition of the mother and the foetus, excessive stress/anxiety of the mother, etc.);—[Shanklin D. R. and Cooke R. J. (1993); Effects of intrauterine growth on intestinal length in the human foetus, *Biol Neonate*, 64:76-81], [Neu, J. (2007); Gastrointestinal development and meeting the nutritional needs of premature infants, *Am. J. Clin. Nutr.*, 85(2): 629S-634S], [Brandãoa, M. C. S. et al., (2003); Effects of pre- and postnatal protein energy deprivation on the myenteric plexus of the small intestine: a morphometric study in weanling rats, *Nutr. Res.*, 23: 215-223].

Any neonate and young infant showing nervous system growth retardation following for example hypoxemia-ischemia at birth or any other adverse event [Taylor, C. T. and Colgan S. P. (2007); Hypoxia and gastrointestinal disease, *J. Mol. Med. (Berl.)*, 85:1295-300], [Barrett R. D. et al. (2007); Destruction and reconstruction: hypoxia and the developing brain, *Birth Defects Res C Embryo Today*, 81:163-76].

Any neonate and infant showing gastrointestinal dysfunctions (digestive disorders, motility disorders, gastrointestinal reflux, slow gastrointestinal transit, oral feeding intolerance), Hirschsprung's disease, and inflammation affecting the gastrointestinal tract (such as Necrotizing enterocolitis) and obstruction pathologies [Burns A. J. et al. (2009); Development of the enteric nervous system and its role in intestinal motility during fetal and early postnatal stages, *Semin. Pediatr Surg.,* 18(4):196-205].

It is known that, in humans, the neural crest cells, from which the enteric nervous system derives, develop in utero in the foetus very early on after conception (from 7.5 weeks of development) [Burns, A. J. and Thapar, N. (2006); Advances in ontogeny of the enteric nervous system, *Neurogastroenterol. Motil.,* 18, 876-887]. The enteric nervous system has been shown to undergo major changes after birth up until the age of six years old, with more minor changes continuing to occur up until the age of ten years old [Wester, T. et al. (1999); Notable postnatal alterations in the myenteric plexus of normal human bowel, *Gut,* 44:666-674]. Thus, if the foetus, neonate or infant has experienced nervous system growth retardation, it is desirable that this retardation be reversed quickly so that the nervous system development "catches up" to a normal level. It is desirable that any damage caused to the enteric nervous system be repaired as quickly as possible, so that the growing foetus or infant experiences as little as possible any gastrointestinal dysfunctions or other pathologies associated with an immature or damaged enteric nervous system.

Thus, the healthy development of the enteric nervous system in the foetus, neonate and growing child helps to control correct establishment and maintenance of the gut motility, gut barrier function, and thus the absorption and digestion functions of the gut. This prevents inflammatory pathological states associated with intestinal dysfunction as well as decreasing the risk of infection and allergy (Neunlist et al. 2008)

Thus, peri-, and/or postnatal interventions correspond to a promising approach to ensure the healthy development of the enteric nervous system. Interventions during pregnancy/lactation may have considerable advantages in terms of convenience and compliance compared to child-directed interventions.

There is a need to promote and support the healthy development and/or repair of the enteric nervous system at the earliest possible stage during gestation as well as during the early phases of their newborn life, when the nervous system is rapidly maturing. Because the nervous system continues to develop during the early years of childhood (up until the age of approximately ten years old), this need for continued support exists throughout this period.

There is, in particular, a need to support the healthy development of the enteric nervous system in the neonates, infants and young children, in order to best prepare them for gastrointestinal challenges such as changes of diet, chemical (for instance medication) or physical (abrasion) injuries, infections, inflammatory/immune reactions, etc., as well as to enhance the future maturation of their enteric nervous system during later life.

There is a need to provide such support or such related composition in a form that is well accepted by the subject population, in particular those of in these populations that are the most fragile or the most in need. There is a further need to not induce disadvantages, side-effects or negatives in such population. There is a need to provide such solutions to the subject populations in the most simple and most cost-effective way.

The present invention applies to all mammals, including animals and humans.

SUMMARY OF THE INVENTION

The invention relates to the use of sweet whey protein (SWP) for promoting the healthy development and/or repair of the enteric nervous system in neonates. The sweet whey protein may be modified sweet whey protein (MSWP), from which caseino-glyco-macropeptide (CGMP) has been removed. The SWP may be partially or extensively hydrolyzed.

The administration of the sweet whey protein, promotes normal and healthy neuronal and glial development in the intestine. It also ensures healthy neuronal differentiation in the peripheral nervous system. Thus, administration of the SWP according to the invention prevents and treats disorders associated with an immature or impaired enteric nervous system. The administration of the SWP according to the invention promotes the healthy development and/or repair of the enteric nervous system in young mammals.

The disorder may be gut barrier dysfunction, food intolerance, or necrotizing enterocolitis. The disorder may be one that is directly associated with gut barrier dysfunction. More generally, the disorder may be a dysfunctional gastrointestinal motility which may be manifested as slow intestinal transit, intestinal discomfort, hard stools, constipation and/or gastrointestinal reflux.

The administration of the sweet whey protein may be to a foetus via the mother. It may also be to a pre-term or term-born infant either directly or via mothers' milk. The administration may be also be to a child, generally up to the age of six years old, or the equivalent age in an animal.

The sweet whey protein may be administered directly to the infant or toddler in its pure form, or diluted in water or breast milk, in a food supplement, or together with in a milk fortifier, or any milk support used during trophic feeding, in an infant formula, or in a milk based drink. The sweet whey protein is administered to the infant, or young child as a daily dose of 30 to 80%, preferably 60% w/w, of the total protein intake.

The administration period for the foetus is generally at least one week, preferably two weeks, more preferably at least one month, and the administration period for the infant or young child is generally at least 4 weeks, preferably 2-12 months, and more preferably at least 18 months and even more preferably up until the child is six years old.

The MSWP may be administered to a pre-term or term-born infant, or child or young adult as a dose of 1.6-3.2 g protein/100 kca, preferably, 1.6-2.2 g protein/100 kca, and more preferably 1.8-2.1 g protein/100 kcal. In one embodiment the MSWP is administered to the infant as a dose of 1.0 to less than 1.6 g protein/100 kcal.

The invention relates to a composition comprising 30-80%, preferably 60% sweet whey protein, for the prevention or treatment of disorders associated with an immature or impaired enteric nervous system in a young mammal.

The invention relates to the use of SWP, and more particularly compositions comprising 30-80% w/w SWP, to promote the healthy development and/or repair of the enteric nervous system in young mammals.

BRIEF DESCRIPTION OF THE DRAWINGS

FIG. 1 Electrical field stimulation of the ex-vivo contractile response in the jejunum:

Tensions (area under the curve (AUC)) obtained by isometric contractions of jejunum in response to electrical field stimulation at 10 Hz in CTRL-w, PR-w and PR pups supplemented with different milk fractions, as measured at sacrifice (post-natal day 14). Results are medians±SEMedian, n=6 to 10 depending on the group, P<0.05. * vs. CTRL-W and t vs. PR-W. Abbreviations are PR: protein restriction; W: water; MSWP28: modified sweet whey P28; GF concentrate: Growth factor concentrate.

FIG. 2 Acetylcholine stimulation of the ex-vivo contractile response in the jejunum:

Tensions (area under the curve (AUC)) obtained by isometric contractions of jejunum in response to acetylcholine at concentration of $10^{-6}$ M in CTRL-w, PR-W and PR pups supplemented with different milk fractions, as measured at sacrifice (post-natal day 14). Results are medians±SEMedian, n=6 to 10 depending on the group, P<0.05; * vs. CTRL-W and t vs. PR-W. Abbreviations are PR: protein restriction; W: water; MSWP28: modified sweet whey P28; GF concentrate: Growth factor concentrate.

DETAILED DESCRIPTION

Definitions

In this specification, the following terms have the following meanings:

"Infants": according to the Commission Directive 2006/141/EC of 22 Dec. 2006 on infant formulae and follow-on formulae, article 1.2 (a), the term "infants" means children under the age of 12 months.

"Neonate" generally means an infant up until the age of 6 months.

"Pre-term infant" generally means an infant born before 37 weeks gestation.

"Term born infant" generally means an infant born after 37 weeks gestation.

"Toddler" generally means a child from when he can walk up to three years old.

"Young child" generally means a child from the age of one up to ten years old (and the equivalent age in animals where the term "young mammals" is used).

"Modified Sweet Whey Protein" (MSWP) or "Modified Sweet Whey" (MSW) means sweet whey protein from which some or all of the caseino-glyco-macropeptide (CGMP) has been removed. In various embodiments of the invention the MSW is depleted by more than 60%, more than 75%, more than 90%, more than 95% or more than 99% (w/w) of its caseino-glyco-macropeptide (CGMP) in comparison to the amount present in average in native sweet whey of the same origin (for example bovine sweet whey).

"Probiotic" means microbial cell preparations or components of microbial cells with a beneficial effect on the health or well-being of the host. [Salminen, S. et al. (1999); Probiotics: how should they be defined, *Trends Food Sci. Technol.*, 10 107-10]. The definition of probiotic is generally admitted and in line with the WHO definition. The probiotic can comprise a unique strain of micro-organism, a mix of various strains and/or a mix of various bacterial species and genera. In case of mixtures, the singular term "probiotic" can still be used to designate the probiotic mixture or preparation. For the purpose of the present invention, micro-organisms of the genus *Lactobacillus* are considered as probiotics.

"Prebiotic" generally means a non-digestible food ingredient that beneficially affects the host by selectively stimulating the growth and/or activity of micro-organisms present in the gut of the host, and thus attempts to improve host health.

"Allergy" means an allergy which has been detected by a medical doctor and which can be treated occasionally or in a more durable manner. A "food allergy" is an allergy with respect to a nutritional composition.

"Infant formulae": according to the Commission Directives 2006/141/EC of 22 Dec. 2006 and/or 91/321/EEC of 14 May 1991 on infant formulae and follow-on formulae, article 1.2 (c), the term "infant formulae" means foodstuffs intended for particular nutritional use by infants during the first four to six months of life and satisfying by themselves the nutritional requirements of this category of persons. It has to be understood that infants can be fed solely with infant formulas, or that the infant formula can be used by the carrier as a complement of human milk. It is synonymous to the widely used expression "starter formula".

"Follow-on formulae": according to the Commission Directives 2006/141/EC of 22 Dec. 2006 and/or 91/321/EEC of 14 May 1991 on infant formulae and follow-on formulae, article 1.2 (d), the term "follow-on formulae" means foodstuffs intended for particular nutritional use by infants aged over four months and constituting the principal liquid element in a progressively diversified diet of this category of persons.

"Growing-up milk": milk-based nutritional composition especially adapted to a child of between one year and three years old.

"Human Milk fortifier": Nutritional composition for infants or young children intended to be added to or diluted with human milk.

The term "hypoallergenic composition" means a composition which is unlikely to cause allergic reactions.

The term "sialylated oligosaccharide" means an oligosaccharide having a sialic acid residue.

The term "fucosylated oligosaccharide" means an oligosaccharide having a fucose residue.

All percentages are by weight unless otherwise stated.

As used in this specification, the words "comprises", "comprising", and similar words, are not to be interpreted in an exclusive or exhaustive sense. In other words, they are intended to mean "including, but not limited to".

Any reference to prior art documents in this specification is not to be considered an admission that such prior art is widely known or forms part of the common general knowledge in the field.

Dietary protein provides the essential amino acids necessary for protein synthesis and growth and protein quality is as important as protein quantity. The present invention provides sweet whey protein, for use by administration for the promotion of the healthy development of the mammalian enteric nervous system. The sweet whey may be obtained from cheese making, particularly the sweet whey obtained after the coagulation of casein by rennet.

The sweet whey protein of the invention comprises 30%-100% w/w protein, preferably >80% w/w protein, more preferably at least 88% w/w protein. An example the SWP that may be used according to the invention is a SWP sold under the trade name, Lacprodan Di9224™. Thus, the SWP may be in the form of a sweet whey protein isolate or a sweet whey protein concentrate.

According to one embodiment of the invention the sweet whey protein is a modified sweet whey fraction, that is, a sweet whey protein which has a reduced level of caseino-glyco-macropeptide (CGMP) compared to classical sweet whey protein. This sweet whey fraction is termed Modified Sweet Whey (MSW). A classical sweet whey can contain from 4 to 40% of CGMP according to the milk processing. This sweet whey fraction, namely, Modified Sweet Whey (MSW), has a CGMP content of up to 40% w/w.

The protein fraction in cows' milk is a mixture of several proteins, which all have a different amino acid profile. Caseino-glyco-macropeptide (CGMP) is derived from the proteolysis of kappa-casein into para-kappa-casein, an insoluble fraction that remains in the casein fraction and CGMP, a soluble fraction that is found in the whey fraction. This reduced CGMP whey fraction or MSW provides the advantage of a reduced threonine content and an increased tryptophan content as compared to normal sweet whey and is therefore suitable as a protein source for infants.

This sweet whey fraction may be further treated to remove minerals (cations, anions), lactose, or any of these substances. The sweet whey may be concentrated as desired. Suitable sweet whey sources are commercially available.

The removal of caseino-glyco-macropeptide may be accomplished by any suitable process. One suitable process is described in EP0880902. In this process, the pH of the sweet whey is adjusted to 1 to 4.3, if necessary. The sweet whey is then contacted with a weakly anionic resin which is predominantly alkaline until the pH of the sweet whey stabilises at about 4.5 to 5.5. The sweet whey fraction from which a significant quantity of the caseino-glyco-macropeptide has been removed, is then collected. According to one embodiment of the invention this reduced CGMP whey protein fraction contains approximately 28% protein, of which CGMP accounts for 2 to 3% of total protein, and is thus termed "MSWP28".

The MSW for use according to the invention may, of course, contain a higher percentage of protein than in MSWP28, for example from 30 to 99%, protein. Similarly, the MSW for use according to the invention may also contain a higher percentage of CGMP than in MSWP28, for example up to 15, 20, 25 or 35% of the total protein.

According to another embodiment of the invention the sweet whey protein is not modified and comprises a minimum of 50% protein. For example the SWP sold under the trade name, Lacprodan Di9224™ by Arla Foods Ingredients, Skanderborgvej 277, 8260 Viby J, Denmark. contains 87% protein.

Other examples of commercially available non-modified sweet whey protein for use according to the invention are Lacprodan DI-8790, another sweet whey from Arla, 894 Instantised, and MPC 485 commercialized by Fonterra (New Zealand), YV0608, Armor Protéines (France) and BiPro, Davisco Food International inc (US, 11000 West 78th Street, Suite 210, Eden Prairie, Minn. 55344).

The sweet whey protein maybe non-hydrolysed. Alternatively according to some embodiments of the invention, the sweet whey fraction protein is partially or extensively hydrolysed to prevent allergic reactions in infants at risk of allergy and to make the protein easier to digest. The hydrolysis process may be carried out as desired and as is known in the art. In general, the whey protein hydrolysate is prepared by enzymatically hydrolysing the sweet whey fraction in one or more steps. For example, for an extensively hydrolysed protein, the sweet whey proteins may be subjected to triple hydrolysis using, for example, Alcalase 2.4 L (EC 940459), then Neutrase 0.5 L (available from Novo Nordisk Ferment AG) and then pancreatin at 55° C. Alternatively, for a less hydrolysed protein, the sweet whey may be subjected to double hydrolysis using, for example, NOVOZYMES and then pancreatin.

If the sweet whey protein used is substantially lactose free, it is found that the protein is subjected to much less lysine blockage during the hydrolysis process. This enables the extent of lysine blockage to be reduced from about 15% by weight of total lysine to less than about 10% by weight of lysine; for example about 7% by weight of lysine. This greatly improves the nutritional quality of the protein source.

The administration of the SWP may be to a foetus via the mother. It may also be to a pre-term or term-born infant either directly or via mothers' milk. The administration may be also be to a young child, generally up to the age of four years old, or the equivalent age in an animal.

The administration of the SWP to the young mammal, which may be human (foetus, infant, toddler or young child) or animal has a positive effect on the development of their enteric nervous system, allowing the system to mature and develop normally. Thus, administration of the sweet whey protein according to the invention prevents and treats disorders associated with an immature or impaired enteric nervous system.

These disorders may be, for example, gut barrier dysfunction, gut barrier dysfunction or necrotizing enterocolitis. These latter states increase risk of infection and allergy, thus leading to food intolerance (therefore need of parenteral nutritional support). More generally, these disorders may be a dysfunctional gastrointestinal motility which may be manifested as slow intestinal transit, intestinal discomfort, hard stools, constipation and/or gastrointestinal reflux.

The beneficial effect of the invention is especially aimed at those young mammals who have experienced, for example, intra uterine growth retardation (IUGR) that may have occurred following any adverse event during the gestation (for example, active or passive smoking of the mother, medication of the mother, low-placenta quality, abnormal placenta positioning, malnutrition of the mother and/or the foetus, etc).

The present inventors have found that SWP and/or SWP containing compositions of the present invention may be used to promote neuronal cell development, functionality, survival, plasticity and differentiation and to protect neuronal cells against degeneration, as shown by promotion of the expression of proteins associated with these biological activities. Such degeneration may follow, for example, any stress situations, such as those affecting the foetus (in utero) such as IUGR, mentioned above, or the newborns (hypoxia-ischemia at birth, oxygen therapy and hyperoxia, inflammation, need for parenteral support, etc.), or any cause leading to oxidative stress. SWP was found to promote neuronal survival and/or limit or prevent neuronal death of enteric neuronal cells, and to promote neuronal growth which is important, for example, in developmental processes.

In infants, the SWP and/or the SWP containing compositions of the present inventions may be used to protect the enteric nervous system from any stress, e.g., occurring during the neuronal development period, and—consequently—to limit and/or prevent stress-induced neuronal growth retardation and associated intestinal dysfunctions.

Thus, SWP may be administered, in the context of the present invention, when there has been already observed a retardation in the development of the enteric nervous system or, prophylactically, when no such retardation has as yet been observed.

The beneficial effect of SWP on the healthy development of the mammalian enteric nervous system is elaborated upon in the paragraphs below.

Doses of SWP:

The sweet whey protein may be administered to infant, or young child as a dose of 1.6-3.2 g protein/100 kca, preferably 1.6-2.2 g protein/100 kca, and even more preferably 1.8-2.1 g protein/100 kcal.

For preterm born babies there are specific recommendations, published by the ESPGHAN Committee on Nutrition, on the amount of protein that they should receive. For the case for preterm babies born weighing less than 1 kg, the recommended protein content intake is 3.6 to 4.1 g protein/100 kcal. For infants born with a birthweight of between 1 to 1.8 kg, the recommended protein content intake is 3.2 to 3.6 g protein/100 kcal [Agostini et al (2010) JPGN 2010 (50), 1, Enteral Nutrient Supply for Preterm Infants].

Thus, the amount of SWP administered to the pre-term infant is appropriately adapted according to the current recommendations. For example, if according to one embodiment of the invention the SWP has a protein content of 100%, and the SWP represents 80% of the total protein being administered to the preterm infant, then a suitable quantity of SWP to be administered to the preterm infant is 2.8-3.2 g per 100 kcal for infants of less than 1 kg and 2.5-2.9 for infants of 1 kg-1.8 kg body weight.

The dose of SWP administered is such that the protein intake of the subject is within the appropriate guidelines (for example, WHO or ESPGHAN committee recommendations).

For example, in a preferred embodiment a composition comprises about 9.0 to about 10.0 w/w % of protein, more preferably about 9.5% w/w %. This corresponds to about 1.8 g protein/100 kcal. An advantage provided by this concentration of protein is that it is equivalent to the amount of protein generally present in human milk and it corresponds to the lower limit described in the *Codex Alimentarius*.

Generally, the MSWP may represent between about 70 to about 100% of the total protein in the composition. Thus, it may also represent 75%, 80%, 85%, 90%, or 95% of the protein in the composition.

Thus, the modified sweet whey protein of the invention may be generally administered to an infant or young child as a dose of 1.6-3.2 g protein/100 kca, preferably 1.6-2.2 g protein/100 kca and even more preferably 1.8-2.1 g protein/100 kcal.

Method of Administration:
(i) Administration to Infants:

The SWP may be administered orally directly to the infants alone (pure or diluted in water or mother's milk for example) as a food supplement (for example, as, or together with a human milk fortifier supplement), or any milk support used during trophic feeding, or as a pharmaceutical or nutraceutical composition, or as an ingredient in an infant milk formula. Such a formula may be an infant "preterm formula" if the progeny is born before term or has a low birth weight, a "starter formula" or a "follow-on formula". The formula may also be an hypoallergenic (HA) formula in which the cow milk proteins are hydrolysed. An example of such starter formula is given in Example 2. The SWP may be administered as a growing-up milk or in any milk-based drink.

(ii) Administration to Young Children:

The SWP may also be administered orally to young children in the form of a pharmaceutical or nutraceutical composition, growing-up milk, milk based drinks, food supplements, milk based yoghurts, desserts and puddings, biscuits and cereal bars, cereals and fruit-based drinks.

(iii) Administration to Expectant or Lactating Mothers:

The SWP may also be administered to expectant or lactating mothers orally, preferably in foods, drinks, dietary supplements or pharmaceutical compositions.

(iv) Administration to Animals:

The SWP may also be administered orally to animals alone, or in water or in the form of a food supplement, a pharmaceutical or nutraceutical composition, or milk or pet food.

Administration with Other Compounds:

The SWP can be administered alone (pure, or diluted in water or milk, including breast milk for example) or in a mixture with other compounds (such as dietary supplements, nutritional supplements, medicines, carriers, flavours, digestible or non-digestible ingredients). Vitamins and minerals are examples of typical dietary supplements. In a preferred embodiment, SWP is administered in a composition, for example, an infant formula, together with other compounds that enhance the described beneficial effect on the young mammals. For example this may be a probiotic Other probiotics may be administered also. Preferably, the probiotic may be selected for this purpose from the group consisting of *Bifidobacterium, Lactobacillus, Lactococcus, Enterococcus, Streptococcus, Kluyveromyces, Saccharoymces, Candida*, in particular selected from the group consisting of *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus lactis, Lactobacillus rhamnosus, Lactobacillus johnsonii, Lactobacillus plantarum, Lactobacillus salivarius, Lactococcus lactis, Enterococcus faecium, Saccharomyces cerevisiae, Saccharomyces boulardii* or mixtures thereof, preferably selected from the group consisting of *Bifidobacterium longum* NCC3001 (ATCC BAA-999), *Bifidobacterium longum* NCC2705 (CNCM I-2618), *Bifidobacterium longum* NCC490 (CNCM I-2170), *Bifidobacterium lactis* NCC2818 (CNCM I-3446), *Bifidobacterium breve* strain A, *Lactobacillus paracasei* NCC2461 (CNCM I-2116), *Lactobacillus johnsonii* NCC533 (CNCM I-1225), *Lactobacillus rhamnosus* GG (ATCC53103), *Lactobacillus rhamnosus* NCC4007 (CGMCC 1.3724), *Enterococcus faecium* SF 68 (NCC2768; NCIMB10415), and mixtures thereof.

Other examples of synergistic compounds that may be included in the compositions, especially infant formula, of the invention are prebiotic compounds. A prebiotic is a non-digestible food ingredient that beneficially affects the host by selectively stimulating the growth and/or activity of one or a limited number of bacteria in the colon, and thus improves host health. Such ingredients are non-digestible in the sense that they are not broken down and absorbed in the stomach or small intestine and thus pass intact to the colon, where they are selectively fermented by the beneficial bacteria. Examples of prebiotics include certain oligosaccharides, such as fructo-oligosaccharides (FOS), cow milk oligosaccharides (CMOS), and galactooligosaccharides (GOS). A combination of prebiotics may be used such as 90% GOS with 10% short chain fructo-oligosaccharides such as the product sold under the trade mark Raftilose® or 10% inulin such as the product sold under the trade mark Raftiline®. Other examples of prebiotics that can be used in the context of the present invention include the group of oligosaccharides obtained from milk or other sources, optionally containing sialic acid, fructose, fucose, galactose or mannose. Preferred prebiotics are sialo-oligosaccharides (SOS), fructo-oligosaccharides (FOS), galacto-oligosaccharides (GOS), isomalto-oligosaccharides (IMO), xylo-oligosaccharides (XOS), arabino-xylo oligosaccharides (AXOS), mannan oligosaccharides (MOS), oligosaccharides of soy, glycosylsucrose (GS), lactosucrose (LS), sialyl-lactose (SL), fucosyl-lactose (FL), Lacto-N-Neotetraose (LNNT), lactulose (LA), palatinose-oligosaccharides (PAO), malto-oligosaccharides, gums and/or hydrolysates thereof, pectins, starches, and/or hydrolysates thereof. An infant formula according to the invention preferably further contains at least one prebiotic in an amount of 0.3 to 10% of the total weight of the dry composition.

In particular, the human milk oligosaccharides, for example sialylated oligosaccharides, described in WO 2012/069416 published on May 31, 2012 may be included in the composition according to the invention. The latter oligosaccharides may act in synergy with the SWP of the invention to promote the healthy development of the mammalian enteric nervous system in the infant or young child.

The daily doses of carbohydrates, and all other compounds administered with the SWP should always comply with the published safety guidelines and regulatory requirements. This is particularly important with respect to the administration to new-born babies, especially those born with low birth weight, very low or extremely low birth weight.

A composition, for example infant formula, containing the SWP for administration according to one embodiment of the invention may contain a further protein source in an amount so that the total protein is not more than 4.0, 3.0 or 2.0 g/100 kcal, preferably 1.8 to 2.0 g/100 kcal. It is preferred that over 50% by weight of the protein source is whey, which includes the modified sweet whey (MSW) and/or unmodified sweet whey. The type of additional protein source is not believed to be critical to the present invention provided that the minimum requirements for essential amino acid content are met and satisfactory growth is ensured although. In one embodiment, the protein content is between 30% and 80% whey proteins. Thus, additional protein sources such as skimmed milk, casein or soy may be used. In one embodiment the casein/whey ratio is between 70/30 and 20/80.

The proteins may be intact or hydrolysed or a mixture of intact and hydrolysed proteins. It may be desirable to supply partially hydrolysed proteins (degree of hydrolysis between 2 and 20%), for example for infants believed to be at risk of developing cows' milk allergy. If hydrolysed proteins are required, the hydrolysis process may be carried out as desired and as is known in the art.

The composition may also comprise a source of carbohydrates and/or a source of fat. The infant formula may contain a source of lipids. The lipid source may be any lipid or fat which is suitable for use in infant formulas. Preferred fat sources include palm oil, high oleic sunflower oil and high oleic safflower oil. The essential fatty acids, linoleic and a-linolenic acid may also be added. One or more essential long chain fatty acids (LC-PUFAs) may be included in the composition. Examples of LC-PUFAs that may be added are docosahexaenoic acid (DHA) and arachidonic acid (AA). The LC-PUFAs may be added at concentrations so that they constitute greater than 0.01% of the fatty acids present in the composition. They may be added as small amounts of oils containing high quantities of pre-formed arachidonic acid and docosahexaenoic acid such as fish oils or microbial oils. Palmitic acid may be added, preferably in the Sn-2 position. In total, the fat content is preferably such as to contribute between 30 to 55% of the total energy of the formula. The fat source preferably has a ratio of n-6 to n-3 fatty acids of about 5: 1 to about 15: 1; for example about 8: 1 to about 10: 1. The maximum fat content in the modified sweet whey fraction is 0.2% w/w.

An additional source of carbohydrate may be added to the nutritional composition. It preferably provides about 40% to about 80% of the energy of the nutritional composition. Any suitable carbohydrate may be used, for example sucrose, lactose, glucose, fructose, corn syrup solids, maltodextrin, or a mixture thereof.

Additional dietary fibre may also be added if desired. If added, it preferably comprises up to about 5% of the energy of the nutritional composition. The additional dietary fibre may be from any suitable origin, including for example soy, pea, oat, pectin, guar gum, acacia gum, oligosaccharides including FOS, GOS and those described above, or a mixture thereof. Suitable vitamins and minerals may be included in the nutritional composition in an amount to meet the appropriate guidelines.

Examples of minerals, vitamins and other nutrients optionally present in the infant formula include vitamin A, vitamin B1, vitamin B2, vitamin B6, vitamin B 12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

The infant formula may optionally contain other substances which may have a beneficial effect such as fibres, lactoferrin, nucleotides, nucleosides, and the like.

One or more food grade emulsifiers may be included in the nutritional composition if desired; for example diacetyl tartaric acid esters of mono- and di-glycerides, lecithin and mono- or di-glycerides or a mixture thereof. Similarly suitable salts and/or stabilisers may be included. Flavours can be added to the composition.

Administration Period:

The duration of the administration may vary. While positive effects are expected with relatively short duration of administration (for example, daily administration during one to two weeks for newborns), longer durations are believed to provide an enhanced effect, or, at least, to maintain the effect in older infants (for example, a duration of three, five, eight or 12 months) or in children (for example, a duration up to the age of 2 or 4 or 6 years old). For administration to animals, the corresponding durations apply.

The expectant mother may start to take the modified sweet whey protein or a standard (unmodified) sweet whey protein as soon as she is aware of her pregnancy. However, the administration period may also start before pregnancy starts, for example if the female is trying to become pregnant. Administration may start at any time after the pregnancy starts. It may start preferably, at month 3, 4, 5, 6, 7 or 8 of the pregnancy, in the case of human pregnancy, or in corresponding periods for other mammals, or up to two weeks before the expected delivery date.

The period of administration can be continuous (for example, up to and including lactation up to weaning), or discontinuous. Continuous administration is preferred for a more sustained effect. However, it is speculated that a discontinuous pattern (for example, daily administration during one week per month, or during alternate weeks) can induce positive effects on the progeny.

The administration may cover at least part of the gestation period and at least part of the lactation period, or the equivalent period should the newborn not be breastfed. Preferably, the administration period to the expectant mother covers substantially the full length of the gestation period, although this may be less. Similarly, the administration period for the lactating mother preferably covers substantially the full length of the lactation period, although, again, this period may be less.

Preferably, the administration to the mother is by daily intake (to be taken once or twice a day), or weekly intake (to be taken one or twice a week).

The modified sweet whey protein or standard sweet whey protein may be administered to the infant directly. This is the case particularly if the mother does not breastfeed or after she discontinues breastfeeding. However, an infant who is being breastfed may also receive the modified sweet whey protein or standard sweet whey protein by direct administration.

Preferably, the administration to the infant is by daily intake. For example, if the modified sweet whey protein or sweet whey protein is administered as an infant formula, the administration is with each feed, i.e. about four to about six times daily for infants, the number of feeds reducing with age. For young children (older than one year), the administration may be less, once or twice a day. For toddlers and children up to the age of six the administration is as milk consumption is advised for growth and development.

The administration to the infant, either via breastfeeding, or by direct administration, or both methods, may be continued up until the age of six months or even one year or longer. Thus, the modified sweet whey protein or standard sweet whey protein may be administered during lactation if lactation takes place, or after partial or full weaning. Administration may continue through the toddler stage and even, up until the age of six years old. It is known that the enteric nervous system continues to develop in children until this latter age [Wester, T. et al. (1999); Notable postnatal alterations in the myenteric plexus of normal human bowel, Gut, 44:666-674]. Thus, the present inventors speculate that the administration of the modified sweet whey protein or standard sweet whey protein may continue to have a positive effect, generally up until six years old.

Effect of Administration of the MSWP or Standard SWP:

Modified sweet whey or standard sweet whey protein administered to neonates promotes the healthy development of the enteric nervous system. In a rat model experiment detailed in Example 1 the effect of the administration of a modified sweet whey (MSWP28) or a commercially available sweet whey protein (Lacprodan Di9224) on neuronal development was evaluated.

In this experiment, pups which had experienced maternal diet-induced intrauterine growth retardation (PR group) and pups which had not experienced IUGR (CTRL) were supplemented, from 2 days after birth, with water (controls; namely CTRL-w and PR-w) or one of the following milk fractions:

Lacprodan Di9224: Whey protein isolate, sweet whey, commercialized by Arla Foods Ingredients, Netherlands.

MSWP28: Sweet whey modified using a Nestle proprietary process (removal of cGMP).

GF concentrate: Growth factor concentrate, which is a high protein isolate (97% proteins) extracted directly from skim milk and commercialized by Tatua (Tatuani, New Zealand). It contains high levels of IGFs and TGFs.

They were administered to pups as isonitrogeneous supplementations (12% proteins), so that the biological effect can be attributed to the qualitative content of the whey fraction rather than the quantity of proteins.

The volume of supplementations was gradually adapted to match the growth of rat pups (150 µl/100 g body-weight). Thus, the supplementation provided from 1 to 5 mg of proteins per day and per pup.

The groups were as follow:
1) CTRL-w: CTRL pups born from CTRL dams, receiving a supplementation of water.
2) PR-w: PR pups born from PR dams, receiving a supplementation of water.
3) PR-Lacprodan Di9224: PR pups born from PR dams, receiving a supplementation of Lacprodan Di9224.
4) PR-MSWP28: PR pups born from PR dams, receiving a supplementation of MSWP28.
6) PR-GF concentrate: PR pups born from PR dams, receiving a supplementation of GF concentrate.

Two weeks after birth, at sacrifice, the neuronal development of the pups was evaluated using two methods: (i) a targeted gene expression profiling approach in jejunum, and (ii) by measuring the ex-vivo contractile response of jejunum to an electrical field stimulation (EFS). The latter method measures the contractile response induced by the enteric nervous system, and, therefore, the maturation and functional degree of the enteric nervous system.

The ex-vivo contractile response of jejunum to acetylcholine was also evaluated, this measures the intestinal muscle contractile response itself, which therefore reflects the maturation and functional degree of the intestinal muscle. The latter experiment was performed as a control, to allow the inventors to separate the factors, i.e. nervous system and muscle, controlling the measured contractile responses.

Ex-Vivo Contractile Response to EFS of Jejunum:

In order to evaluate the neuronal maturation in the protein restriction model and following supplementation with the sweet whey isolates of the invention, the contractile response of the jejunum to EFS, which measures the implication/capacity of the neuronal network to stimulate the muscle contractility, was measured. The possible implication of any effect on intestinal muscular maturation due to the protein restriction, or following supplementation with sweet whey isolates, was evaluated by measuring the contractile response of jejunum to acetylcholine.

Figure 1:
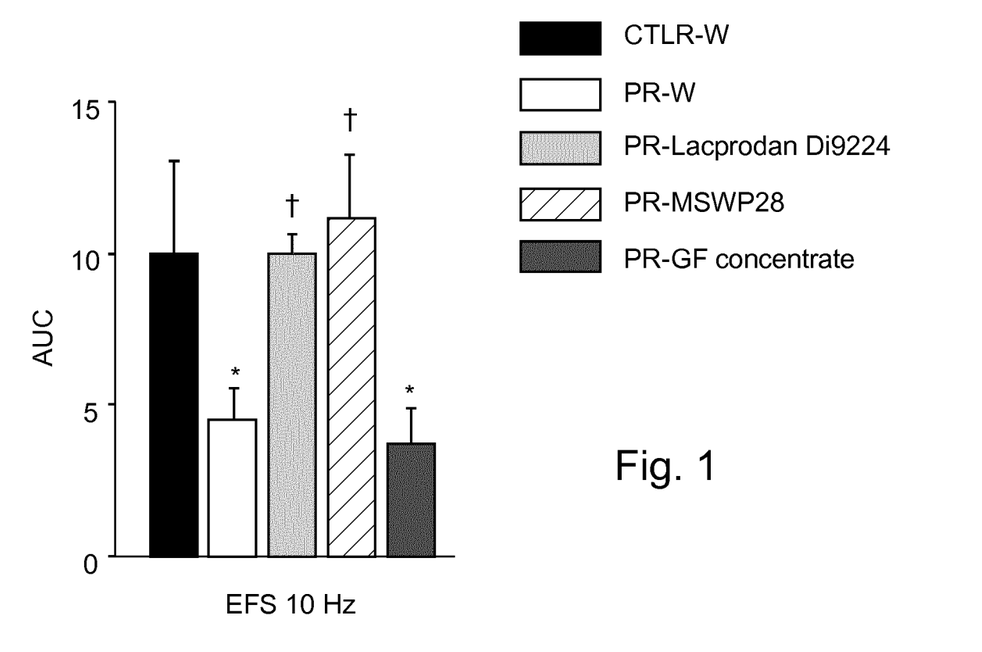
Figure 2:
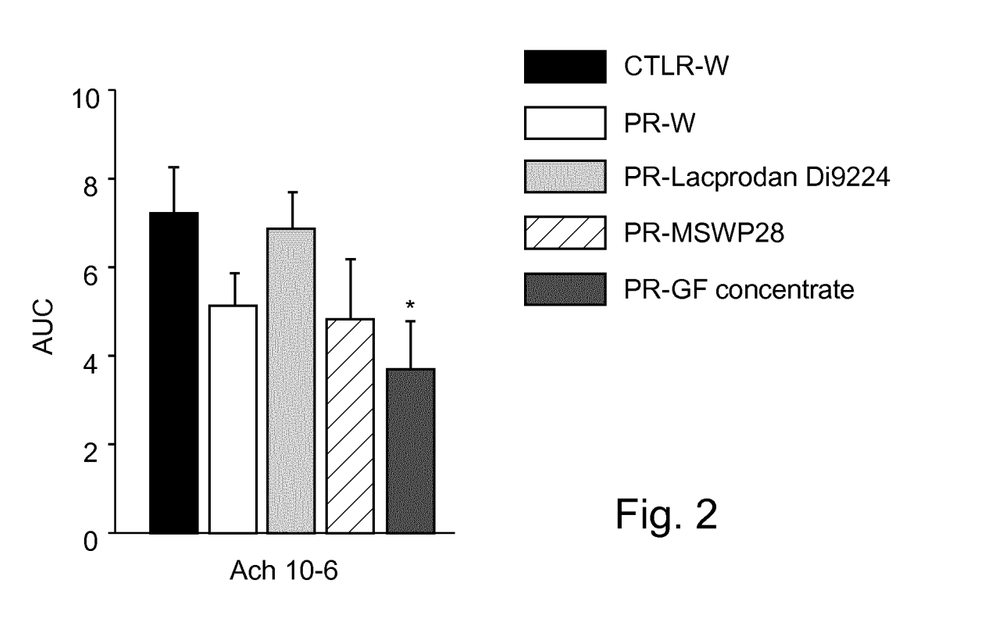

The jejunum contractile response to EFS was reduced in PR-w as compared to CTRL-w at the frequency of 10 Hz (P=0.040) (FIG. 1). The jejunum contractile response to acetylcholine was slightly reduced, but not significantly (P=0.181), in PR-w as compared to CTRL-w (FIG. 2). Taken together, this reflects an impaired neuro-muscular interaction, and, in particular, an impaired neuronal maturation, in the jejunum of protein restricted pups.

The supplementation with sweet whey fractions (Lacprodan Di9224 and MSWP28) significantly increased (P=0.007 and 0.026 respectively) the contractile response of the jejunum at 10 Hz to a level statistically similar to controls (FIG. 1). This indicates a promoting effect of sweet whey fractions on the neuronal stimulatory capacity in the jejunum, which reflects a promotion of the neuronal development and function in the neonatal period. The maturation of the jejunum muscle compartment was indeed not significantly modified following the sweet whey fraction supplementation (P=0.199 and 0.828 for Lacprodan Di9224 and MSW P28, respectively) since the jejunum contractile response capacity to acetylcholine remained unchanged as compared to PR-w (FIG. 2).

Taken together, these data indicate that standard and modified sweet whey protein (Lacprodan Di9224 and MSWP28, respectively in the experiment) improve the neuronal-mediated muscle contractile response to EFS in the jejunum of PR pups. This indicates that sweet whey protein promotes the postnatal development and functionality of the enteric nervous system.

Such a stimulatory effect was not observed in response to acetylcholine stimulation, suggesting no improvement of smooth muscle contractile response to acetylcholine, i.e. no promotion of the smooth muscle postnatal maturation.

These data therefore clearly show a beneficial effect of sweet whey protein in promoting neuronal development and function during the postnatal period. Based on these data, sweet whey constitutes a new nutritional solution to prevent or treat disorders associated with an immature and/or impaired enteric nervous system in young mammals up to the age of about six years in particular during the neonatal period (generally defined as the first 6 months of life, for a human).

Expression of Genes Involved in the Gut Neuronal Development:

In the rat model experiment of Example 1, the effect of protein restriction, as well as protein restriction followed by milk fraction supplementation, on the expression of major genes involved in neuronal development biological pathways was studied in the jejunum, using a gene expression profiling approach. The genes studied are listed in Table 2 and the data are presented in Table 3. Data from genes only poorly or not expressed are not reported. Among the remaining 35 genes expressed at a detectable level, a significant interaction between the treatment (protein restriction) and the supplementation (milk fractions) was observed for 18 of them (Table 3). Genes that were significantly differentially expressed are those mainly involved in the maturation or differentiation of neurons and glial cells, or are markers of neuronal growth and plasticity.

The present inventors have previously shown (Cettour and Faure, manuscript in preparation) that compensatory mechanisms take place in protein restricted pups (PR) to help promote the cellular and neuronal development in the small intestine. The present data confirm these findings. Specifically, the gene expression of neurotrophic factors and their receptors, such as NGF (Nerve Growth Factor), Gfra1 (GDNF family receptor alpha 1), Gfra2 (GDNF family receptor alpha 2), Ntf4 (Neurotrophin 4), S100B (S100 calcium binding protein B) and synaptophysin, were significantly up-regulated in the PR-w group as compared to the CTRL-w group. This likely reflects a disequilibrium and a "stress" situation in the animals, which remains nevertheless insufficient to promote the neuronal maturation as indicated by our results following EFS stimulation.

The supplementation with Lacprodan Di9224 significantly increased the gene expression of NGF, NGFr (Nerve Growth Factor receptor) and Chrm3 (muscarinic receptor 3) and decreased that of S100b to a level of expression similar to CTRL-w (Table 3). The increased gene expression of NGFr and NGF, together with the increased expression of NGF in PR, suggests the promotion of neuronal growth, development and survival observed in FIG. 1 [Tessarollo, (1998) Pleiotropic functions of neurotrophins in development. *Cytokine Growth Factor Rev.* 9(2):125-37]. It is noted that that levels of NGF and NGFr increased in the PR-w as compared to CTRL-w, but that this increase was significant only for NGF.

The supplementation with MSWP28 significantly increased the gene expression of Crhr1, ApoE, NGFr, Ntf3 (neurotrophin 3), Chrm2 and 3 (muscarinic receptor 2 & 3), and TGFb2, and significantly decreased that of S100b. Again, the increased gene expression of NGFr and Ntf3 may contribute to promote neuronal growth and development, and can, at least in part, explain the neuronal maturation observed in FIG. 1.

The muscarinic receptors as encoded by Chrm2 & Chrm3 gene are involved in the intestinal muscle contractility and motility in response to Acetylcholine [Chen J, Wen J, Cai W. (2012) Smooth muscle adaptation and recovery of contractility after massive small bowel resection in rats. Exp Biol Med (Maywood). May 1; 237(5):578-84]. Similarly, Corticotropin releasing hormone receptor (Crhr), also known as corticotropin releasing factor, and apolipoprotein E are involved in muscle contraction and motility pathways [Taché Y, Kiank C, Stengel A. (2009) A role for corticotropin-releasing factor in functional gastrointestinal disorders Curr Gastroenterol Rep. August; 11(4):270-7; Vincelette J, Martin-McNulty B, Vergona R, Sullivan M E, Wang Y X, (2006) Reduced cardiac functional reserve in apolipoprotein E knockout mice Transl Res. July; 148(1):30-6.)].

Following MSWP28 supplementation, the expression of chrm3 and that of the previously mentioned genes involved in muscle contractility pathways were significantly increased as compared to PR-w. This could suggest the promotion of the intestinal muscle maturation, but this would deserve further attention since these increased gene expression were however not yet translated into a measurable functional benefit as indicated by the unchanged contractility response to acetylcholine at time of pup's sacrifice (FIG. 2).

The supplementation with the growth factor concentrate significantly increased the gene expression of Crhr1 and significantly decreased that of GDNF, GFra1, Neurod1, S100b, and Syp. In contrast to MSWP 28 and Lacprodan Di 9224, no increased expression levels of the NGF pathway (nerve growth factor pathway) was observed following the supplementation with the growth factor concentrate. This is coherent with the result that no beneficial effect was observed on the neuronal mediated contractile response (EFS) of jejunum (FIG. 1) upon supplementation with GF1.

The gene expression level of NGFr was significantly up-regulated following the supplementation with either MSWP28 or LacprodanDi9224, while the increased gene expression induced by the protein restriction was maintained in these supplemented groups. This clearly indicates the stimulation of the NGF pathway.

Neurotrophins, like NGF, and their receptors are highly expressed in the peripheral and central nervous system. Gene targeting approaches in the mouse have documented the role of neurotrophines in promoting the developmental maturation of neurons of the peripheral and central nervous system, confirming their critical role in neuronal development. Reviewed in Tessarollo, L. (1998). NGF is also critical for the survival and maintenance of sympathetic and sensory neurons. Without it, these neurons undergo apoptosis [Freeman R S et al., (2004) *NGF deprivation-induced gene expression: after ten years, where do we stand?* "NGF and Related Molecules in Health and Disease". *Prog. Brain Res.* Progress in Brain Research 146: 111-26]. Nerve growth factor causes axonal growth. There is evidence that NGF circulates throughout the entire body and is important for maintaining homeostasis. [Levi-Montalcini R (2004). "The nerve growth factor and the neuroscience chess board". *Prog. Brain Res.* 146: 525-7.] Human and bovine milk also contain NGF activity suggested to play a role in the postnatal neurodevelopment and neuroprotection of the newborn

[Gaull, G. E., Wright, C. E. & Isaacs, C. E. (1985). Significance of growth modulators in human milk. *Pediatrics.* 75: 142-145].

The modifications of gene expression observed in Table 3, and, in particular, the stimulation of the NGF pathway, likely contribute to the observed promotion of the neuronal stimulatory responses to EFS in the groups supplemented with MSW P28 and Lacprodan showed in FIG. 1.

Populations that may benefit from the invention are:

Preterm infants, low birth weight (<2500 g), very low birth weight infants (<1500 g) and extremely low birth weight infants (<1000 g);

Premature or term-born infants having experienced an intrauterine growth retardation (IUGR) that occurred following any adverse events during gestation;

Any neonate and infant showing nervous system growth retardation following for example hypoxemia-ischemia at birth or any other adverse event;

Any neonate and infant or child up to the age of six with gastrointestinal dysfunctions (digestive disorders, motility disorders, gastrointestinal reflux, slow gastrointestinal transit, oral feeding intolerance), Hirschsprung's disease, and inflammation affecting the gastrointestinal tract (such as necrotizing enterocolitis) and obstruction pathologies.

The invention is further described with reference to the following examples. It will be appreciated that the invention as claimed is not intended to be limited in any way by these examples.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

Example 1

Animal Study

Feeding and Sacrifice

Animal experiments were conducted under authorization n° 2120 granted by the Office Vétérinaire Cantonal, Etat de Vaud. Two-month-old female Sprague-Dawley rats were obtained after one week of gestation from Harlan, Barcelona. On the day of their arrival, rat dams were placed in individual cages and randomly assigned either to control (CTRL) or protein restricted (PR) groups. Animals had access to food and water ad libitum and were maintained in a 12 hr light/dark cycle.

The diets of CTRL and PR dams are detailed in Table 1. CTRL dams received a control diet containing 20% of proteins (casein) fitting standard rat protein requirement during gestation (Reeves, P. G., Nielsen, F. H., Fahey, G. C., JR. 1993. AIN-93 Purified Diets for Laboratory Rodents: Final Report of the American Institute of Nutrition Ad Hoc Writing Committee on the Reformulation of the AIN-76A Rodent Diet. J. Nutr. 123:1939-1951.) PR dams received a PR diet containing 10% of proteins (casein). Both diets were iso-caloric, the protein deficit being balanced by addition of corn starch.

TABLE 1

Composition of control (CTRL) and protein restricted (PR) AIN-93G diets

| Components | Diets | |
|---|---|---|
| | CTRL | PR |
| Cornstarch | 53 | 63 |
| Caseine (K-Caseinate) | 20 | 10 |
| Sucrose | 10 | 10 |
| Soybean oil | 7 | 7 |
| Cellulose | 5 | 5 |
| Mineral mix AIN-93G | 4 | — |
| Mineral mix AIN-93M | — | 4 |
| Vitamin mix AIN-93 | 1 | 1 |
| Choline Bitartrate | 0.25 | 0.25 |
| L-Cysteine | 0.3 | 0.3 |
| Tert-buthylhydroquinone | 0.0014 | 0.0014 |

CTRL and PR dams received their respective diets during both gestation and lactation until the day of sacrifice (postnatal day 14 (PND 14)).

On PND 2, pups were randomly assigned to dams from the same experimental group, and litter size was adjusted to 9 pups per dam with a minimal number of four to five males per litter.

From PND 2 till PND14, a daily hand/pipette feeding supplementation of water or one of the following milk fractions was administered to control or treated groups, respectively. The volume of supplementations was gradually adapted to match the growth of rat pups (150 µl/100 g body-weight).

The groups and diets were as follow:
1) CTRL-w: CTRL pups born from CTRL dams, receiving a supplementation of water.
2) PR-w: PR pups born from PR dams, receiving a supplementation of water.
3) PR-Lacprodan Di9224: PR pups born from PR dams, receiving a supplementation of Lacprodan Di9224.
4) PR-MSWP28: PR pups born from PR dams, receiving a supplementation of MSWP28.
5) PR-GF concentrate: PR pups born from PR dams, receiving a supplementation of GF concentrate.

The milk fractions were:
Lacprodan Di9224: Whey protein isolate, sweet whey, commercialized by Arla Foods Ingredients, Denmark.
MSWP28: Sweet whey modified using a Nestle proprietary process (removal of cGMP).
GF concentrate: Growth factor concentrate commercialized by Tatua, New Zealand. It contains enriched levels of IGFs and TGFs.

At PND 14, a maximum of 10 pups from CTRL and PR groups were weighed and then sacrificed by decapitation after halothane anaesthesia.

The peritoneal cavity was opened by longitudinal incision of the abdominal wall and the whole gastrointestinal tract was removed and freed from mesentery. The first ⅓ of the jejunum segment following the Treitz ligament was isolated and divided into several segments. One segment was flushed with PBS at room temperature and placed in cold Krebs' solution for ex-vivo contractile response measurements. One segment was rinsed with ice cold PBS to remove luminal material, transferred to individual cryotubes, snap frozen in liquid nitrogen and kept at −80° C. until gene analysis was carried out.

The neuronal development in jejunum was evaluated using two methods: (i) a targeted gene expression profiling approach, and (ii) by measuring the ex-vivo contractile response of jejunum to electrical field stimulation (EFS).

Ex-Vivo Contractile Response of Jejunum to Electrical Field Stimulation (EFS):

Approximately 1 cm length segments of distal jejunum were placed in cold Krebs' solution ($CaCl_2$ (5 mM), $MgCl_2.6H_2O$ (1.2 mM), NaCl (120 mM), $NaH_2PO_4.H_2O$ (1.2 mM), $NaHCO_3$ (15.5 mM), KCl (5.9 mM), phenol red (0.005 mM) and glucose (11.5 mM)) pre-oxygenated with 95% $O_2$/5% $CO_2$. The intestinal segments were suspended along their longitudinal axis in a tissue bath (50 ml volume) filled with Krebs solution oxygenated with 95% $O_2$/5% $CO_2$, at 37° C. One end of the muscle was attached to a stationary clamp. The other end was attached via an inelastic wire to an isometric force transducer.

A stabilization period of 30 min was allowed to obtain spontaneous contractions. The tissue was then stretched to an initial length such that any further stretch would increase tension at rest. Isometric contractility in the distal jejunum was induced by acetylcholine (Ach, $10^{-5}$ M) or by electrical field stimulation (EFS, 5-10 Hz). Ach was applied for 1 min. After completion of the dose-response curve, the strips were tested with 80 mM KCl to assure that they had maintained their ability to contract. The signals were digitally recorded on a computer using Powerlab Chart 3.4. The results were normalized by cross-sectional area after carefully blotting and weighing the tissue fragments. Non-linear fittings were performed using Prism 4.0 (GraphPad Software, Inc., San Diego, USA). To obtain the frequencies, an analysis of the power density spectra of the measured signal was carried out. A high pass filter, with a cut off frequency of 2 Hz (much smaller than the Nyquist frequency of 100 Hz) was applied. The Welch method was used for the computation of the power spectrum density with 1.3 seconds of overlapping, imposing a low frequency discretization: a series of frequencies was defined between 0 and 2 Hz, equally spaced by 0.05 Hz. The calculations of the power spectrum density were made using the Goertzel algorithm. Three frequencies corresponding to the three largest power values below 2 Hz were chosen.

Gene Expression Profiling:

Total RNA were extracted from jejunum of PR and CTRL pups using the phenol/chloroform method with the TriPure® (Roche Diagnostics, Basel, Switzerland) reagent according to the manufacturer instructions. Briefly, frozen tissue samples (50-100 mg) were homogenized in 1 ml of TriPure® using the TissueLyser (Qiagen AG, Basel, Switzerland). Quantity and quality of the isolated RNA were measured using the RiboGreen RNA quantification kit (Invitrogen-Molecular Probes, Carlsbad, Calif.) and the RNA 6000 Nano LabChip kit (Agilent Technologies) according to the instructions provided with the kits. The reverse transcription was performed using an oligo (dT15) primer (Promega, Madison, Wis.) and the ImProm-II™ reverse transcription system (Promega) according to the instructions provided by the manufacturer, with 1 µg total RNA.

TABLE 2

List of genes analysed.

| Gene Symbol | Official Full Name | Function |
| --- | --- | --- |
| Ache | Acetylcholinesterase | Motility |
| Crhr2 | Corticotropin releasing hormone receptor 2 | Motility |
| Bdnf | Brain derived neurotrophic factor | Neurotrophic factor |
| Chat | Choline acetyltransferase | Motility |
| Cckar | Cholecystokinin A receptor | Motility |
| Chrm2 | Cholinergic receptor, muscarinic 2 | Motility |
| Chrm3 | Cholinergic receptor, muscarinic 3 | Motility |
| Crh | Corticotropin releasing hormone | Motility |
| Crhbp | Corticotropin releasing hormone binding protein | Motility |
| Crhr1 | Corticotropin releasing hormone receptor 1 | Motility |
| Egf | Epidermal growth factor | Growth factor |
| Apoe | Apolipoprotein E | Motility |
| Gap43 | Growth associated protein 43 | Neuronal maturation |
| Gdnf | Glial cell derived neurotrophic factor | Glial Maturation |
| Gfap | Glial fibrillary acidic protein | Glial Maturation |
| Gfra1 | GDNF family receptor alpha 1 | Glial Maturation |
| Gfra2 | GDNF family receptor alpha 2 | Glial Maturation |
| Gmfb | Glia maturation factor, beta | Glial Maturation |
| Gmfg | Glia maturation factor, gamma | Glial Maturation |
| Igf1 | Insulin-like growth factor 1 | Growth & neurotrophic factor |
| Igf2 | Insulin-like growth factor 2 | Growth & neurotrophic factor |
| Lep | Leptin | Neurotrophic factor |
| Neurod1 | Neurogenic differentiation 1 | Neurodifferenciation |
| Npffr2 | Neuropeptide FF receptor 2 | Neuronal maturation factor |
| Ngf | Nerve growth factor (beta polypeptide) | Neurotrophic factor |
| Ngfr | Nerve growth factor receptor (TNFR superfamily, member 16) | Neurotrophic receptor |
| Ngfrap1 | Nerve growth factor receptor (TNFRSF16) associated protein 1 | Neurotrophic receptor |
| Npy | Neuropeptide Y | Motility |
| Npy1r | Neuropeptide Y receptor Y1 | Motility |
| Npy2r | Neuropeptide Y receptor Y2 | Motility |
| Nrg1 | Neuregulin 1 | Neurodifferenciation |
| Nrg2 | Neuregulin 2 | Neurodifferenciation |
| Ntf3 | Neurotrophin 3 | Neurotrophic factor |
| Ntf4 | Neurotrophin 4 | Neurotrophic factor |
| Ntrk1 | Neurotrophic tyrosine kinase, receptor, type 1 | Neurotrophic receptor |
| Ntrk2 | Neurotrophic tyrosine kinase, receptor, type 2 | Neurotrophic receptor |
| S100b | S100 calcium binding protein B | Neurotrophic factor |
| Syp | Synaptophysin | Neurodevelopment |
| Tacr1 | Tachykinin receptor 1 | Motility |
| Tgfa | Transforming growth factor alpha | Growth factor |
| tgfb2 | Transforming growth factor beta 2 | Growth factor |

TABLE 2-continued

List of genes analysed.

| Gene Symbol | Official Full Name | Function |
|---|---|---|
| tgfb3 | Transforming growth factor beta 3 | Growth factor |
| Ucn | Urocortin | Motility |
| Actb | Actin, beta | Controls |
| Rpl13a | Ribosomal protein L13A | Controls |
| Rplp1 | Ribosomal protein, large, P1 | Controls |
| Gapdh | Glyceraldehyde-3-phosphate dehydrogenase | Controls |
| RGDC | Rat Genomic DNA Contamination | Controls |

The expression levels of major genes involved in the enteric nervous system development (see Table 2) were assessed by 2-step quantitative real-time RT-PCR using RT Profiler PCR Array System by Sybergreen (SABiosciences). Measurements were carried out in duplicates using specific sets of primers and fluorescent TAMRA probes during the log-linear phase of a PCR reaction with the 7600HT TaqMan Fast Real-Time PCR System (Applied Biosystems) using Sequence Detection Software, version 2.2. The PCR reactions took place within 2-µl wells previously loaded with the specific primers and probes by the manufacturer into each of the 384 wells of the reaction card. The reaction was performed using a final cDNA sample concentration of 0.8 ng/µl with the TaqMan Universal PCR Master Mix (Applied Biosystems) containing the AmpliTaq Gold DNA Polymerase enzymes (Applied Biosystems), the nucleotides and the ROX fluorescent dye used as a passive load reference. The sequences of primers and probes used were designed and validated by Applied Biosystems and were taken from the Assay-on-Demand rat library. The relative expression level of each gene was normalized by the geometric average of control genes (those whose expression was statistically stable across experimental groups in our conditions).

TABLE 3

Expression levels of genes in the *jejunum* of CTRL-w, PR-w and PR pups supplemented with different milk fractions at sacrifice (post natal day 14). The results are means ± SEM, n = 6. Abbreviations are PR: protein restriction; W: water; MSWP28: modified sweet whey P28; GF: Growth factor. Genes poorly or not expressed, and for which no conclusion can be made, are not reported in this table

| | Expression levels | | | | | | | | | |
|---|---|---|---|---|---|---|---|---|---|---|
| | CTRL-w | | PR-w | | PR-LacprodanDi9224 | | PR-MSWP28 | | PR-GF concentrate | |
| | Means | SEM | Means | SEM | Means | SEM | Means | SEM | Means | SEM |
| Crhr1 | 35.0 | 4.5 | 10.8 | 3.6 | 15.0 | 3.9 | 27.7 | 4.6 | 26.7 | 2.7 |
| Apoe | 580.6 | 54.9 | 993.4 | 133.9 | 948.2 | 54.4 | 1017.7 | 178.9 | 834.7 | 128.0 |
| Gap43 | 128.3 | 19.2 | 199.4 | 51.3 | 195.5 | 29.0 | 184.4 | 32.9 | 126.2 | 19.5 |
| Gdnf | 4.3 | 0.4 | 11.4 | 1.2 | 8.0 | 1.0 | 8.1 | 0.9 | 3.8 | 0.7 |
| Gfra1 | 11.3 | 1.1 | 25.4 | 2.7 | 16.6 | 2.0 | 15.1 | 1.9 | 11.2 | 1.6 |
| Gfra2 | 33.1 | 3.5 | 49.6 | 5.6 | 57.1 | 2.9 | 59.8 | 6.0 | 47.8 | 7.1 |
| Gmfb | 351.4 | 37.6 | 242.7 | 23.0 | 240.8 | 14.0 | 342.1 | 33.9 | 374.3 | 55.9 |
| Gmfg | 202.5 | 18.3 | 208.7 | 21.0 | 160.8 | 12.8 | 192.2 | 14.4 | 203.4 | 29.0 |
| Igf1 | 7.6 | 0.7 | 10.5 | 1.5 | 10.5 | 1.1 | 14.9 | 1.8 | 8.0 | 1.8 |
| Igf2 | 183.4 | 26.4 | 103.4 | 46.5 | 65.0 | 23.0 | 59.5 | 53.4 | 31.2 | 32.5 |
| Neurod1 | 15.2 | 1.5 | 16.7 | 1.8 | 14.1 | 1.7 | 13.0 | 1.2 | 8.5 | 1.5 |
| Ngf | 0.9 | 0.2 | 1.9 | 0.4 | 2.3 | 0.2 | 1.8 | 0.2 | 1.3 | 0.2 |
| Ngfr | 7.7 | 0.9 | 10.6 | 2.0 | 14.0 | 1.5 | 16.2 | 1.8 | 8.7 | 1.3 |
| Ngfrap1 | 549.5 | 52.6 | 590.9 | 61.6 | 657.7 | 33.4 | 702.1 | 42.3 | 571.7 | 87.0 |
| Npy | 16.4 | 1.7 | 36.4 | 5.9 | 21.7 | 3.8 | 16.1 | 2.8 | 16.6 | 2.4 |
| Nrg1 | 28.4 | 4.6 | 32.2 | 5.0 | 39.8 | 4.0 | 51.6 | 4.5 | 37.5 | 8.0 |
| Nrg2 | 3.2 | 0.5 | 5.6 | 0.8 | 5.3 | 0.6 | 4.2 | 0.5 | 3.8 | 0.5 |
| Ntf3 | 1.6 | 0.1 | 2.0 | 0.4 | 3.2 | 0.6 | 4.1 | 0.7 | 1.8 | 0.6 |
| Ntf4 | 1.0 | 0.1 | 2.0 | 0.1 | 2.1 | 0.2 | 1.6 | 0.2 | 1.6 | 0.2 |
| S100b | 55.3 | 9.0 | 116.2 | 25.3 | 51.9 | 13.6 | 55.4 | 15.1 | 61.2 | 9.8 |
| Syp | 6.0 | 0.5 | 9.0 | 2.1 | 10.3 | 1.3 | 9.3 | 1.0 | 5.3 | 0.9 |
| Tacr1 | 4.7 | 0.5 | 6.5 | 0.3 | 7.1 | 0.9 | 8.3 | 1.0 | 3.1 | 1.0 |
| Tgfa | 6.5 | 1.0 | 5.1 | 0.6 | 5.5 | 0.6 | 7.2 | 1.1 | 3.8 | 0.8 |
| Glucagon | 894.1 | 123.5 | 499.2 | 125.5 | 1198.3 | 231.3 | 899.4 | 128.3 | 498.7 | 0.0 |
| Ache | 14.5 | 2.0 | 12.8 | 3.0 | 9.9 | 1.5 | 13.4 | 2.7 | 15.8 | 3.2 |
| Chrm2 | 7.0 | 0.7 | 9.3 | 0.8 | 10.1 | 1.0 | 13.3 | 1.0 | 10.6 | 0.9 |
| Chrm3 | 1.6 | 0.3 | 1.1 | 0.1 | 2.6 | 0.5 | 3.4 | 0.7 | 2.1 | 0.4 |
| Tgfb2 | 7.1 | 0.4 | 12.4 | 1.2 | 11.6 | 1.0 | 13.5 | 1.2 | 9.9 | 0.8 |
| Tgfb3 | 1.3 | 0.1 | 1.9 | 0.2 | 2.1 | 0.2 | 2.3 | 0.4 | 1.5 | 0.2 |

TABLE 3-continued

Expression levels of genes in the *jejunum* of CTRL-w, PR-w and PR pups supplemented with different milk fractions at sacrifice (post natal day 14). The results are means ± SEM, n = 6. Abbreviations are PR: protein restriction; W: water; MSWP28: modified sweet whey P28; GF: Growth factor. Genes poorly or not expressed, and for which no conclusion can be made, are not reported in this table

| | Analysis of variance Probability levels | | | | | | | |
|---|---|---|---|---|---|---|---|---|
| | Interaction | CTRL-w vs FR-w | CTRL-w vs PR-Lacprodan Di9224 | CTRL-w vs PR-MSWP28 | CTRL-w vs PR-GF conc | PR-w vs PR-Lacprodan Di9224 | PR-w vs PR-MSWP28 | PR-w vs PR-GF conc |
| Crhr1 | 0.004 | 0.003 | 0.043 | NS | NS | NS | 0.003 | 0.001 |
| Apoe | 0.024 | NS | 0.048 | 0.000 | 0.046 | NS | 0.047 | NS |
| Gap43 | 0.060 | NS | NS | NS | NS | NS | NS | NS |
| Gdnf | 0.000 | 0.000 | 0.001 | 0.001 | NS | NS | NS | 0.000 |
| Gfra1 | 0.002 | 0.001 | 0.005 | 0.002 | NS | NS | NS | 0.005 |
| Gfra2 | 0.003 | 0.030 | 0.002 | 0.000 | 0.020 | NS | NS | NS |
| Gmfb | 0.282 | NS | NS | NS | NS | NS | NS | NS |
| Gmfg | 0.417 | NS | NS | NS | NS | NS | NS | NS |
| Igf1 | 0.082 | NS | NS | NS | NS | NS | NS | NS |
| Igf2 | 0.453 | NS | NS | NS | NS | NS | NS | NS |
| Neurod1 | 0.046 | NS | NS | NS | 0.012 | NS | NS | 0.003 |
| Ngf | 0.001 | 0.002 | 0.000 | 0.000 | 0.028 | NS | NS | NS |
| Ngfr | 0.000 | NS | 0.001 | 0.000 | NS | 0.023 | 0.008 | NS |
| Ngfrap1 | 0.457 | NS | NS | NS | NS | NS | NS | NS |
| Npy | 0.207 | NS | NS | NS | NS | NS | NS | NS |
| Nrg1 | 0.428 | NS | NS | NS | NS | NS | NS | NS |
| Nrg2 | 0.108 | NS | NS | NS | NS | NS | NS | NS |
| Ntf3 | 0.008 | NS | 0.020 | 0.001 | NS | NS | 0.003 | NS |
| Ntf4 | 0.001 | 0.003 | 0.000 | 0.000 | 0.001 | NS | NS | NS |
| S100b | 0.026 | 0.002 | NS | NS | NS | 0.013 | 0.040 | 0.048 |
| Syp | 0.010 | 0.019 | 0.020 | 0.018 | NS | NS | NS | 0.031 |
| Tacr1 | 0.014 | NS | NS | 0.017 | NS | NS | NS | NS |
| Tgfa | 0.271 | NS | NS | NS | NS | NS | NS | NS |
| Glucagon | 0.453 | NS | NS | NS | NS | NS | NS | NS |
| Ache | 0.590 | NS | NS | NS | NS | NS | NS | NS |
| Chrm2 | 0.006 | NS | 0.015 | 0.000 | 0.010 | NS | 0.012 | NS |
| Chrm3 | 0.014 | NS | NS | 0.015 | NS | 0.018 | 0.001 | NS |
| Tgfb2 | 0.003 | NS | 0.003 | 0.000 | 0.020 | NS | 0.020 | NS |
| Tgfb3 | 0.003 | NS | 0.003 | 0.000 | 0.020 | NS | 0.020 | NS |

Statistics:

The effect of protein restriction was evaluated by comparing PR with CTRL groups. The effect of the protein-based supplementations were evaluated by comparing each PR-supplemented group with PR-w. An eventual restoration to CTRL levels was evaluated by comparing each PR-supplemented group with the CTRL-w group.

Nonparametric methods were used to analyse the data Wilcoxon rank sum test was used to test the differences between the treatments. Hodges-Lehmann estimate of the pair-wise treatment difference with its 95% confidence interval was also obtained.

For gene expression, the statistical analyses were performed on the raw cycle threshold (Ct) counts, assumed to be log 2 values. A one-way Analysis of Variance (ANOVA) was applied on the change: gene—reference gene, the calculated p-value is the probability that at least one of the groups is different from the others. The calculations have been done on 5 potential house-keeping genes, or on the mean of more than one, only the most stable ones have been kept with the criteria of the least residual error.

Example 2

An example of the composition of an infant formula for use according to the present invention is given below. This composition is given by way of illustration only. The protein source is a mixture of 60% MSWP28 and 40% casein.

| Nutrient | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Prebiotic (100% GOS) (g) | 0.64 | 4.3 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |

-continued

| Nutrient | per 100 kcal | per litre |
|---|---|---|
| Fe (mg) | 1.2 | 8 |
| I (μg) | 15 | 100 |
| Cu (mg) | 0.06 | 0.4 |
| Zn (mg) | 0.75 | 5 |
| *Bifidobacterium longum* BB536 | 2 × 10$^7$ cfu/g of powder | |

The invention claimed is:

1. A method of treating a disorder associated with an immature or impaired enteric nervous system in a young mammal in need thereof, the method comprising administering to the young mammal an effective amount of a composition comprising sweet whey protein in an amount of between 30 wt. % and 80 wt. % of the total protein in the composition, the disorder is selected from the group consisting of (i) gut barrier dysfunction, (ii) food intolerance, (iii) necrotizing enterocolitis, (iv) dysfunctional gastrointestinal motility manifested as at least one of slow intestinal transit, intestinal discomfort, hard stools, constipation or gastrointestinal reflux, and (v) combinations thereof.

2. The method according to claim 1, wherein the sweet whey protein comprises at least 88% w/w protein relative to the sweet whey protein and has a maximum fat content of 0.2% w/w relative to the sweet whey protein and a caseino-glyco-macropeptide (CGMP) content up to 40% w/w relative to the sweet whey protein.

3. The method according to claim 1, wherein the sweet whey protein is a modified sweet whey protein (MSWP) from which caseino-glyco-macropeptide (CGMP) has been partially or entirely removed.

4. The method according to claim 3 wherein the final CGMP content of the MSWP is less than 15% w/w.

5. The method according to claim 1, wherein the sweet whey protein has a degree of hydrolysis of at least 2%.

6. The method according to claim 1, wherein the young mammal is an animal.

7. The method according to claim 1, wherein the young mammal is selected from the group consisting of a human foetus, a pre-term or term-born infant, and a child up to the age of six.

8. The method according to claim 7, wherein administration period to the fetus has a duration of at least one week, and wherein the administration period to the infant or the child has a duration of at least 4 weeks.

9. The method according to claim 1, wherein the young mammal has at least one characteristic selected from the group consisting of (i) the young mammal experienced hypoxemia-ischemia at birth, (ii) the young mammal has experienced or is experiencing an intrauterine growth retardation (IUGR), (iii) the young mammal had or is predicted to have a low, very low or extremely low birth weight, and (iv) the young mammal is suffering or suffered from enteric nervous system growth retardation in utero, during or after birth.

10. The method according to claim 1, wherein administration to the young mammal is by a route selected from the group consisting of (i) indirectly via the lactating mother and (ii) directly to the young mammal.

11. The method according to claim 1, wherein the sweet whey protein is administered directly to the young mammal in a form selected from the group consisting of pure form, diluted in water or breast milk, a food supplement, a milk fortifier, a milk support used during trophic feeding, an infant formula for premature infants, a starter formula, a follow-on formula, a growing-up milk, and a milk based drink.

12. The method according to claim 1, wherein administration is orally.

13. The method according to claim 1, wherein the sweet whey protein is administered to the young mammal as a dose of 1.6-3.2 g protein/100 kcal of the composition.

14. The method according to claim 1, wherein the composition comprises at least one prebiotic.

15. The method according to claim 1, wherein the composition comprises at least one probiotic.

16. The method according to claim 1, wherein the composition is administered in a daily dose comprising an amount of the sweet whey protein that is 60 to 80 wt. % of the total protein intake of the young mammal.

17. The method according to claim 1, wherein the sweet whey protein is between about 70 wt. % and 80 wt. % of the total protein in the composition.

18. The method according to claim 1, wherein the sweet whey protein has a degree of hydrolysis between 2 and 20%.

* * * * *